United States Patent [19]

Huhtala

[11] Patent Number: 5,541,677
[45] Date of Patent: Jul. 30, 1996

[54] SPECTACLES RETAINING STRAP WITH CONNECTED EARPLUGS

[75] Inventor: Keith Huhtala, 1055 Villia Way, Fernley, Nev. 89408

[73] Assignees: Keith Huhtala; Kirk Huhtala, both of Fernley, Nev.

[21] Appl. No.: 366,249

[22] Filed: Dec. 28, 1994

[51] Int. Cl.$^6$ ..................................................... G02C 3/00
[52] U.S. Cl. ........................... 351/156; 351/123; 351/157; 351/158
[58] Field of Search .................................. 351/156, 158, 351/41, 53, 122, 123, 157; D24/106, 174; D16/309, 336, 339; 181/129, 130, 135; 24/3.3; 2/423, 426, 448; 128/864, 865, 866

[56] References Cited

U.S. PATENT DOCUMENTS

| | | | |
|---|---|---|---|
| D. 262,491 | 12/1981 | Ebert | D24/106 |
| 1,997,931 | 4/1935 | Hoey | 128/164 |
| 2,660,092 | 11/1953 | Bloom | 24/3.3 X |
| 3,173,147 | 3/1965 | Gross et al. | 2/14 |
| 3,395,702 | 8/1968 | White | 128/151 |
| 3,807,526 | 4/1974 | Sygnator | 181/33 R |
| 3,871,372 | 3/1975 | Bivins | 128/152 |
| 3,915,166 | 10/1975 | McCrink | 128/152 |
| 3,943,925 | 3/1976 | Leight | 2/423 X |
| 4,037,273 | 7/1977 | Labaire | 2/209 |
| 4,133,604 | 1/1979 | Fuller | 351/123 |
| 4,219,018 | 8/1980 | Draper, Jr. | 128/152 |
| 4,314,553 | 2/1982 | Westerdal | 128/152 |
| 4,541,696 | 9/1985 | Winger et al. | 351/153 |
| 4,671,265 | 6/1987 | Andersson | 128/152 |
| 4,683,587 | 7/1987 | Silverman | 351/158 X |
| 4,727,582 | 2/1988 | de Vries et al. | 381/68.7 |
| 4,751,746 | 6/1988 | Rustin | 2/13 |
| 4,783,164 | 11/1988 | Heiberger | 351/156 |
| 4,896,380 | 1/1990 | Kamitani | 2/428 |
| 4,902,120 | 2/1990 | Weyer | 351/158 |
| 5,074,375 | 12/1991 | Grozil | 128/864 |
| 5,092,667 | 3/1992 | Bagley | 351/156 |
| 5,201,856 | 4/1993 | Edwards | 2/209 |
| 5,249,309 | 10/1993 | Berg et al. | 2/209 |
| 5,278,999 | 1/1994 | Brown et al. | 2/209 |
| 5,404,385 | 4/1995 | Ben-Haim | 377/24.2 |

*Primary Examiner*—William L. Sikes
*Assistant Examiner*—Hung Xuan Dang
*Attorney, Agent, or Firm*—Ken J. Pedersen; Barbara S. Pedersen

[57] ABSTRACT

Embodiments of a vision-hearing protection device are shown and described, each embodiment including an eyeglass retainer, for holding eyeglasses on the user's head or around the neck, and earplugs connected to the retainer for protecting the user's hearing. Preferably, the vision-hearing protection device includes a retraction feature wherein the earplugs may be quickly pulled in toward the retainer for more secure and compact "storage" and then quickly drawn out toward the ears for convenient reinsertion. In the preferred embodiment, the retainer is a hollow tube having three holes. A cord slidably extends through the hollow tube, with the cord ends extending out from the two holes that are nearer the retainer ends to attach to the earplugs, and with the cord middle portion extending out from the third hole in the rear or middle portion of the hollow tube. The middle portion of the cord may be pulled out away from the retainer to pull the earplugs closer to the retainer for storage, or, the earplugs may be pulled away from the retainer for reinsertion in the user's ears.

4 Claims, 3 Drawing Sheets

SPECTACLES RETAINING STRAP WITH CONNECTED EARPLUGS

BACKGROUND OF THE INVENTION

1. Field of the Invention

This invention relates generally to eyeglass retainers, and, more specifically, to retainers that include a means for protection of the user's ears and/or hearing.

2. Related Art

Several combination ear and eye protection systems have been developed. Patents issued to Rustin (U.S. Pat. No. 4,751,746), Bagley (U.S. Pat. No. 5,092,667), and Edwards (U.S. Pat. No. 5,201,856) disclose apparatus for attachment to eyeglasses for shielding and protecting the user's ears, particularly from sun, wind, or cold.

Rustin discloses a cloth panel attached to the eyeglass temple that extends along the side of the user's head to shield the ear. The Rustin apparatus may include a receiving pocket into which the back and top of the ear may be tucked for additional shielding.

Bagley discloses a two-piece headband attached to the temples of eyeglasses and extending around to the back of the user's head. The headband has two tubular sleeve members that extend from the inside surface of the headband to receive and hold the temples.

Edwards discloses an ear protector that extends around the back of the user's head and has sleeves in each of its two opposing ends for slipping over the temples of the glasses. The sleeves grip the temples near the front of the glasses and have an elastomeric material forming a part of the sleeve that clings to the eyeglass temples.

What is still needed is an system that combines efficient protection of the hearing as well as the vision of the user. Many sporting, industrial, workshop, and agricultural environments pose dangers to hearing because of the noise of guns, rotating equipment, saws, farm machinery, etc. These same environments often pose danger to vision because of particulate, chips, chemicals, dirt, or dirty water, etc. that can enter an unprotected eye. Government regulations require that both eye and ear protection be available to workers in many industrial settings.

A common problem for workers and sportsmen is that using both eye and ear protection is inconvenient. The typical earplug wearer takes the earplugs out each time he/she enters a less-noisy area or needs to talk to someone, and then one or more of the earplugs gets lost or dirty from being set down or tucked into a pocket or toolbox. Earplugs are inexpensive and replaceable, but the wearer tires of keeping several sets in his/her pocket or tool-box and tires of dealing with them. In the food industry, corded earplugs, which are earplugs that are connected by a cord or string, are often supplied to the workers so that they may tie or loop the cord through part of a hardhat or cap, thus preventing loose earplugs from falling into food vats. Keeping safety glasses and goggles at hand is also a nuisance for many industrial workers. Unless accustomed to wearing eyeglasses for sight correction, user's too often take off and set down their protective glasses or goggles, sometimes losing or damaging them.

There is a need, therefore, for a device that keeps both eyeglasses and earplugs clean and conveniently reachable during work or sport.

SUMMARY OF THE INVENTION

An object of the present invention is to provide a system combining vision and hearing protection, for the many industrial, farming, and sporting environments that can pose dangers to both eyes and ears. Another object is to provide a system for keeping hearing protection handy and clean, to encourage use of it in work and sporting environments. Another object is to provide this combined hearing and vision protection inexpensively so that it can be made available in large numbers in industrial settings.

The invented vision-hearing protection device comprises an eyeglass retainer and earplugs connected to the retainer. The earplugs are connected to the retainer in such a way that they alternatively may be inserted into the user's ears, or left to hang near the user's head for easy access. The retainer easily and releasably attaches to protective eyewear for hanging the eyewear around the users neck when not in use, so that the eyewear is not lost, or set down or dropped into dirty and damaging areas.

The preferred embodiment of the invention includes an eyeglass retainer that comprises a hollow tube with two ends that slip onto and resiliently grip the ear-pieces of the temples of a pair of glasses or goggles. A cord extends through part of the hollow tube, exiting the hollow tube through two holes that are located in the side portions of the tube. Each end of the cord connects to an earplug, so that the earplugs hang from the retainer.

Preferably, the vision-hearing protection device includes a retraction means wherein the earplugs may be quickly pulled in toward the retainer for more secure and compact "storage" and then quickly drawn out toward the ears for convenient reinsertion. This retraction means allows the user to adjust the location of the earplugs to prevent them from dangling or swinging more than is comfortable and also to place the earplugs in a predictable position for easy and quick grabbing for reinsertion.

The preferred embodiment of the retraction means comprises the cord slidably extending through the hollow tube and extending at its middle portion out from a hole in the rear portion of the hollow tube. The middle portion of the cord may be pulled out away from the retainer to retract the cord ends into the hollow tube, thus pulling or retracting the earplugs closer to the tube. For reinsertion, the user simply reaches for the earplugs and pulls them toward his/her ears, thus drawing the cord ends out from the tube and pulling the middle portion into the tube.

DETAILED DESCRIPTION OF THE PREFERRED EMBODIMENT

Figure 1:
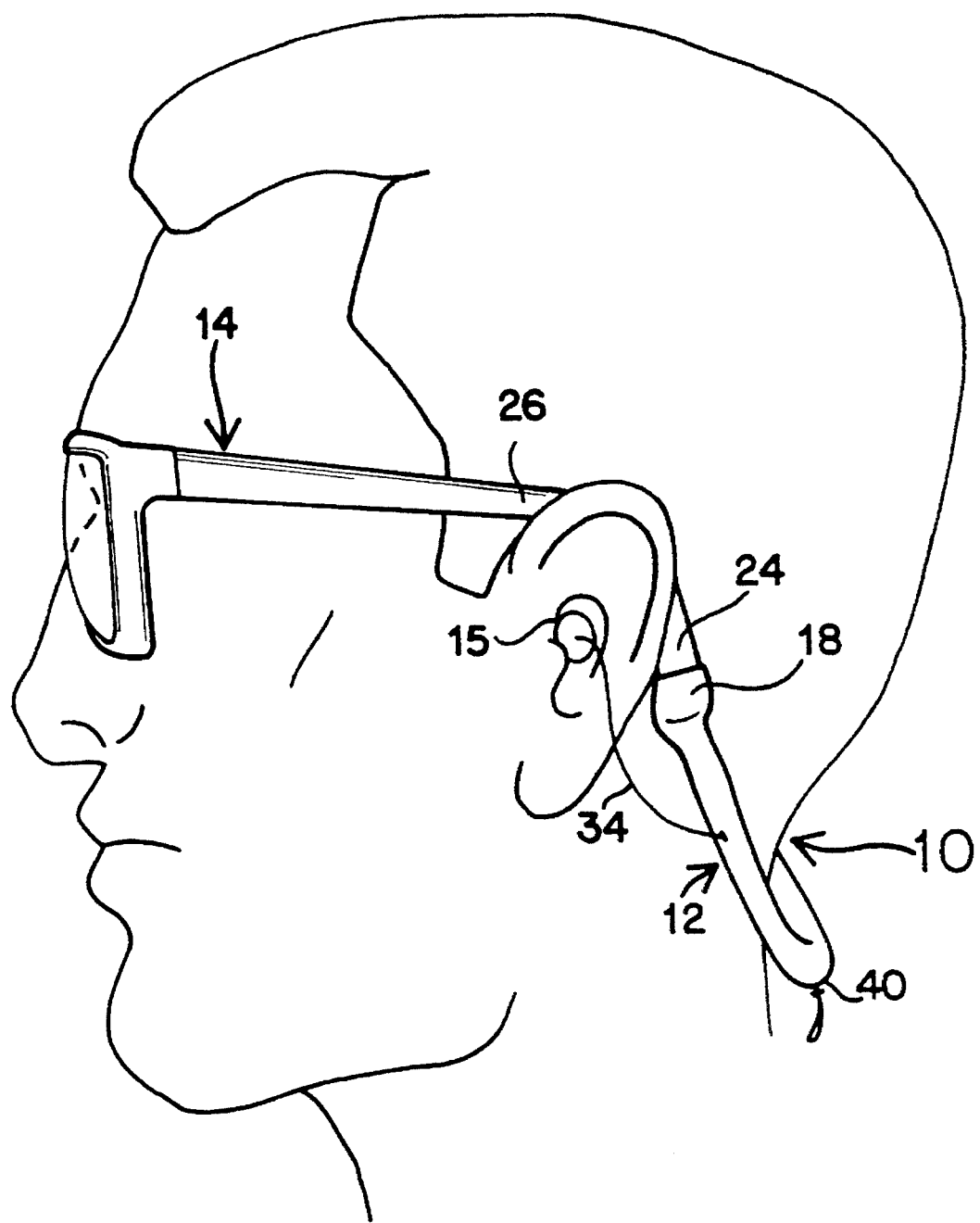
FIG. 1 is a perspective view of one embodiment of the invented vision-hearing protection device in use, with earplugs extended and inserted into the user's ears.
Figure 2:
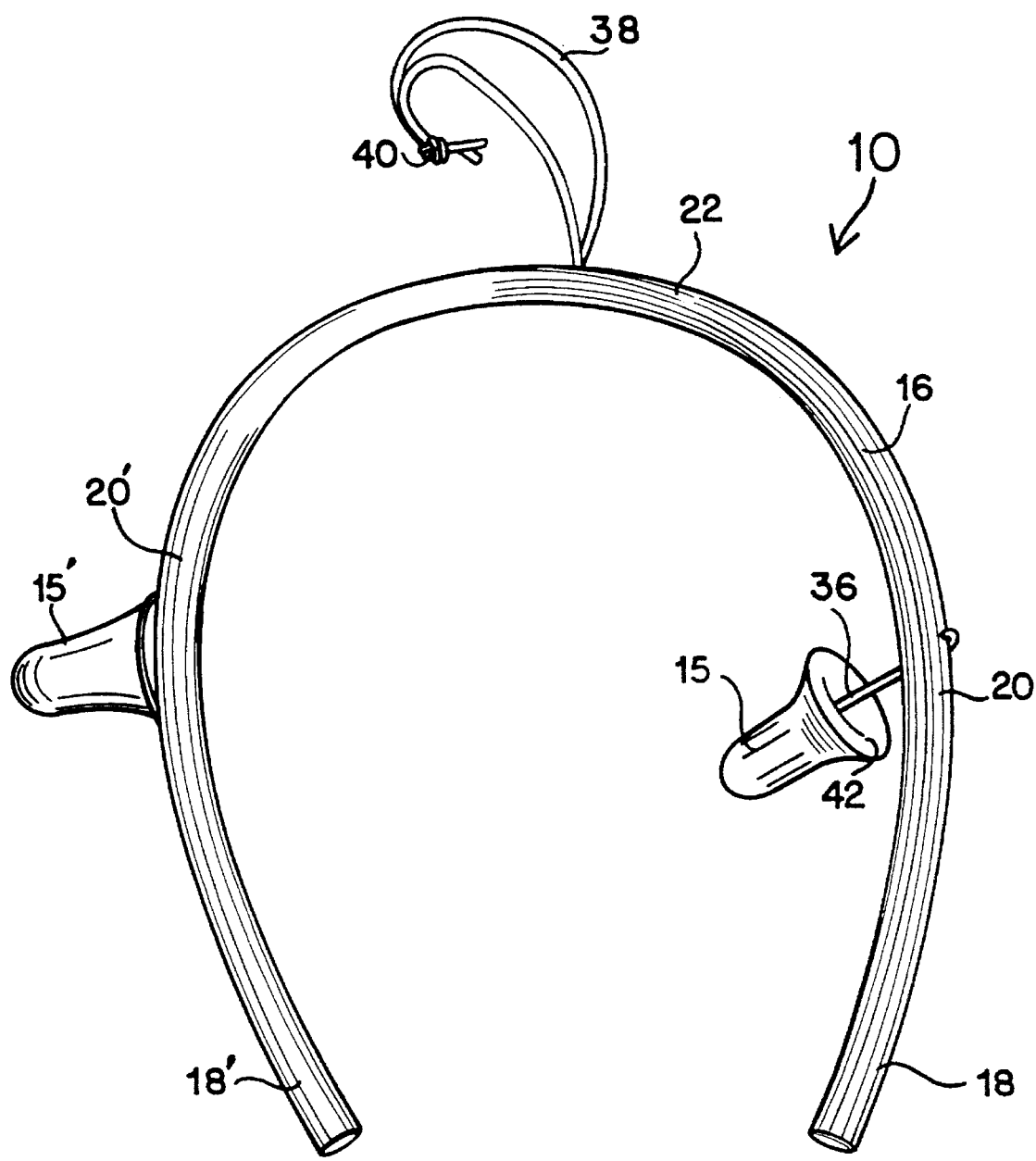
FIG. 2 is a top view of the combined retainer and attached earplugs of the embodiment of FIG. 1, with one earplug being fully retracted and the other earplug retracted to within about 1 inch of the retainer.
Figure 3:
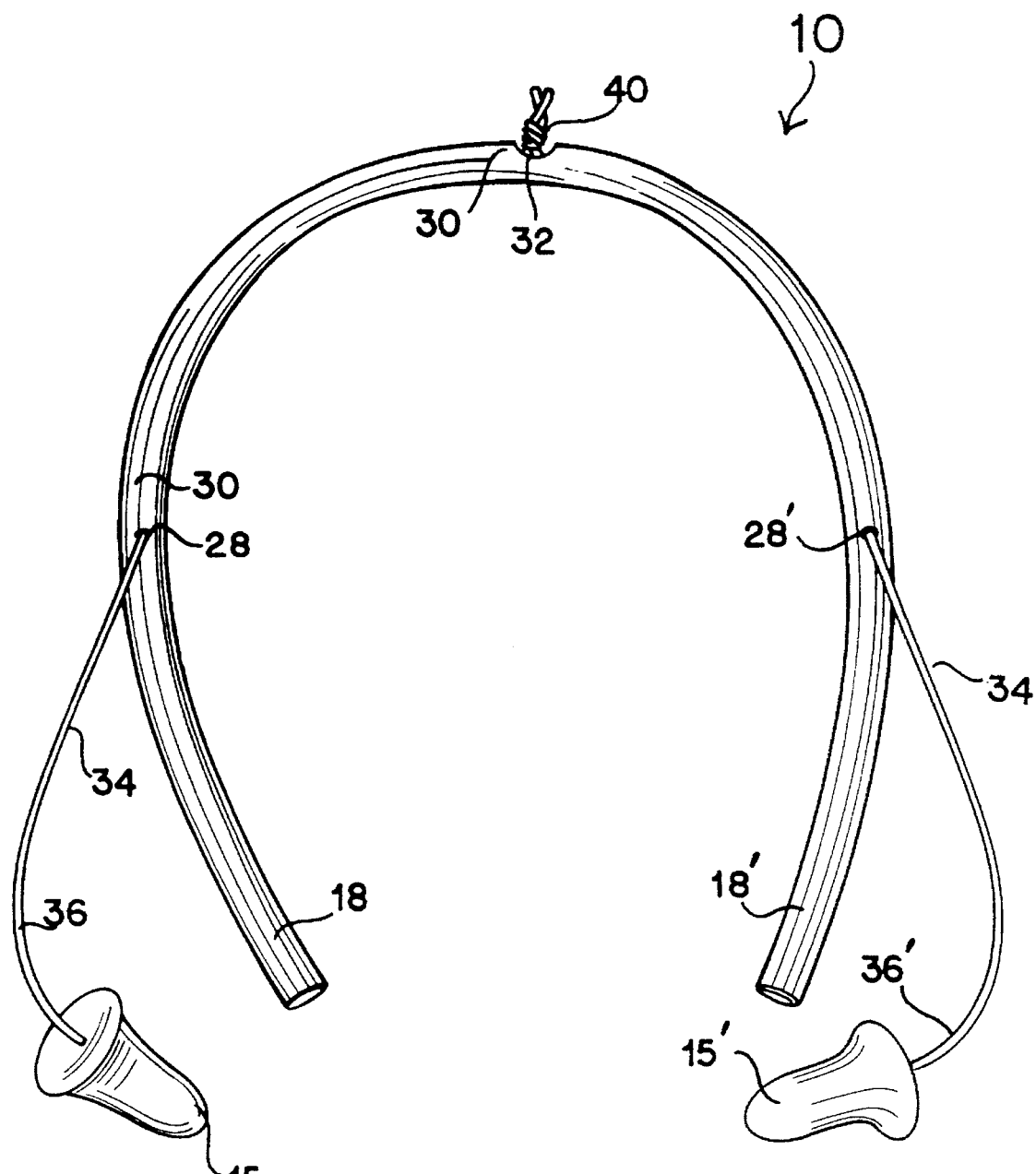
FIG. 3 is a bottom view of the embodiment of FIG. 2, with earplugs extended.

Referring to FIGS. 1–3, there are shown some, but not the only, embodiments of the invented vision-hearing protection device. The protection device 10 comprises a retainer 12 connected to a pair of eyeglasses 14, and a pair of earplugs 15, 15' connected to the retainer 12. Preferably, the eyewear lenses are safety lenses, which are shatterproof in nature for protecting against explosions and impacts. Optionally, any eyewear may be used, for example, sun glasses or normal prescription glasses for less dangerous environments.

The retainer 12 comprises a flexible plastic, hollow tube 16 with a first end 18, second end 18', side portions 20, 20' and a retainer middle portion or rear portion 22 (described as "rear" herein because it is positioned behind the user's head when in use). The hollow tube 16 has an inner diameter smaller than the ear-pieces 24 of the eyeglass temples 26. The first and second ends 18, 18' resiliently stretch over and frictionally engage the ear-pieces 24 for secure but removable connection of the retainer 12 to the eyeglasses 14. The ends 18, 18' are preferably placed over the ear-pieces 24 less than about 1 inch to be secure during normal use, but so that the ends 18, 18' may be removed conveniently by the user and, also, so that the retainer 12 separates from the glasses 14 in an emergency when part of the protection device 10 becomes caught in or on equipment, for example.

The hollow tube 16 has two holes 28, 28' in the tube wall 30 at the side portions 20, 20' and a third hole 32 in the tube wall 30 at the rear portion 22, in between the side holes 28, 28'. Through the side holes 28, 28' a cord 34 or other flexible string is threaded so that the cord ends 36, 36' exit the side holes 28, 28' and connect to the earplugs 15, 15'. Each earplug has a small hole cut into its outer end 42 and the cord end 36, 36' is inserted and glued or fused into the earplug hole. The middle portion 38 of the cord 34 loops out through the rear hole 32 and includes a knot 40, bead, or other retention means so that the middle portion 38 cannot slip completely back into the tube 16 through the rear hole 32.

The preferred protection device 10 includes an earplug retraction means, which adjusts the location of the unused earplugs 15, 15', particularly the distance of the earplugs from the retainer, for the convenience and comfort of the user. By placing the earplugs close to the retainer, preferably within about 1 inch or less from the retainer, the retraction means prevents the earplugs from dangling more than is comfortable to the individual user and prevents the user from groping around to find dangling earplugs. When the user needs hearing protection, the earplugs 15, 15' are readily graspable without looking in the mirror and may be quickly drawn forward for insertion into the ears.

The retraction means comprises the cord 34 sliding back and forth in the hollow tube 16 to move the earplugs 15, 15' relative to the retainer 12. When the middle portion 38 is pulled out away from the retainer 12, the cord 34 slides through the hollow tube 16 toward the rear hole 32, thus pulling the cord ends 36, 36' into the tube 16 and retracting the earplugs 15, 15' to be close to the retainer 12, as shown in FIG. 3. When the earplugs 15, 15' are fully retracted, they abut against the tube wall 30 and are held relatively motionless, as illustrated by ear plug 15' in FIG. 2. When the earplugs 15, 15' or the cord ends 36, 36' are pulled away from the retainer 12, the cord 34 slides through the hollow tube 16 to allow the cord ends 36, 36' to extend out a convenient distance from the retainer 12 to reach to the user's ears, as shown in FIG. 1. Pulling the earplugs out from the retainer retracts the middle portion 38 into the hollow tube 16, lessening the length of loop of cord that extends out from the rear hole 32.

The preferred material for the hollow tube 16 is latex tubing, such as KRATON™ latex tubing, for example, with a 3/16 inch inner diameter and a 3/64 inch tube wall thickness. For the cord 34 and earplugs 15, 15', conventional off-the-shelf corded foam earplugs may be used, such as those available to workers in the food industry. Plastic foam, putty polymer, or silicon earplugs may be used, for example, with various noise reduction ratings. The cord 34 may be nylon or other plastic monofilament cord. Bright colors are preferred for the retainer 12, cord 34, and earplugs. 15, 15' to make the device 10 fashionable, the retainer easily found in a backpack or toolbox, and employee's use of the device 10 readily apparent to industrial safety and management staff.

Alternatively, various retainer styles may be used for the invented protection device. The retainer may be other than a hollow tube, for example, a solid but flexible cord with ends that releasably clip onto eyeglass temples. The retainer may be a style that exerts little or no force on the glasses when the glasses are in place on the user's face, but that acts as a "leash" or "necklace" for hanging the glasses around the user's neck when the glasses are removed, as in the preferred embodiment. Also, elastic-strap retainers may be used, such as those commonly used in sports to strap or secure the glasses to the user's face.

Alternatively, various connection means may be used for connecting the earplugs to the retainer. The connection means may be a string, cord, cloth, spring, or stretchable material that can extend or be drawn out, preferably, but not necessarily, about 4–6 inches from the retainer for easy placement of the plugs in the ears. Optionally, for designs with very flexible retainers of sufficient length, the connection means may be short, taking advantage of the flexibility of the retainer to allow the earplugs to be brought close to the ears. For example, for a very flexible and light-weight retainer, a connection means could be the retainer passing through a hole bored through the end of an earplug.

Alternatively, various earplug styles may be used. Although disposable, compressible foam plugs are preferred, the earplugs may be any material or shape that may be safely inserted into the ears for reducing the noise level reaching the ear-drum.

Alternatively, various retraction means may be used for retracting the earplugs close to the retainer to prevent dangling earplugs from tickling or annoying the user. For example, a retraction means may include separate cords attached to each earplug, with each cord threaded in and out of the retainer tube through two holes in its respective side portion 20, 20 and a knot tied in the end of each cord as it extends from the second of the two holes. In this design, the knotted end of each cord could be pulled back by the user to pull earplugs toward the first of the two holes and the retainer. In this design, each earplug may be retracted independently from the other.

The retainer 12 and connected earplugs 15, 15' may be constructed from a set of conventional corded earplugs and a length of latex tubing. The cord of the corded earplugs is cut in half, and each half of the cord 34 is threaded through its respective hole 28, 28' that is cut through one side of the tube wall 30 in the side portion 20, 20' of the tube 16. To facilitate this threading, a needle may be used to pull the cord through the hollow tube 16 and the needle and cord may be lubricated with silicone or other lubricant. This lubrication, or lubrication that may be placed on the cord at other times, keeps the cord 34 sliding smoothly through the tube 16. The ends of the two cords are then pulled out of the third hole 32 and are tied together to form the knot 40.

The combination hearing and vision protection device 10 may be used in a wide variety of environments, both industrial and recreational. The device 10 may be used to make protection convenient in refineries, chemical plants, saw mills, power plants, mines, etc.. The device 10 may be used for comfort at speedtracks, shooting ranges, and other athletic events, for example, with eyeglasses or sunglasses.

Although this invention has been described above with reference to particular means, materials, dimensions, and embodiments, it is to be understood that the invention is not limited to these disclosed particulars, but extends instead to all equivalents within the scope of the following claims.

I claim:

1. A vision-hearing protection device for installation on a user's eyeglasses, the protection device comprising:

an eyeglass retainer comprising a hollow tube with a tube wall having two holes, said hollow tube having two ends for connection to the eyeglasses and a retainer middle portion between the two ends for extending behind the user's head, two earplugs for insertion into the user's ears, and connection means comprising a cord extending through the hollow tube and having a cord middle portion and two ends, the two ends extending out of the retainer through the two holes and being attached to the earplugs, connecting the earplugs to the retainer.

2. A protection device as set forth in claim 1, wherein the tube wall has a third hole, located between the two holes, through which the cord middle portion extends out from the retainer, for being pulled by the user to pull the cord ends in toward the retainer.

3. A vision-hearing protection device comprising:

eyeglasses having two temples, an eyeglass retainer comprising a hollow tube with a tube wall having two holes, said hollow tube having two ends for connection to the eyeglass temples, and a retainer middle portion between the two ends for extending behind a user's head, two earplugs for insertion into the user's ears, and connection means comprising a cord extending through the hollow tube and having a cord middle portion and two ends, the two ends extending out of the retainer through the two holes and being attached to the earplugs, connecting the earplugs to the retainer.

4. A protection device as set forth in claim 3, wherein the tube wall has a third hole, located between the two holes, through which the cord middle portion extends out from the retainer, for being pulled by the user to pull the cord ends in toward the retainer.

* * * * *